United States Patent [19]

Chen et al.

[11] Patent Number: 5,380,947
[45] Date of Patent: Jan. 10, 1995

[54] DIAMONDOID-CONTAINING AMINES

[75] Inventors: Catherine S. H. Chen, Berkeley Heights, N.J.; Dong-Ming Shen, Langhorne, Pa.; Steven E. Wentzek, East Brunswick, N.J.

[73] Assignee: Mobil Oil Corporation, Fairfax, Va.

[21] Appl. No.: 71,382

[22] Filed: Jun. 4, 1993

Related U.S. Application Data

[63] Continuation-in-part of Ser. No. 943,644, Sep. 11, 1992, Pat. No. 5,256,394.

[51] Int. Cl.$^6$ .................. C07C 211/62; C07C 211/63
[52] U.S. Cl. .................................................. 564/281
[58] Field of Search ..................... 564/281; 514/642

[56] References Cited

PUBLICATIONS

Marxer et al. "Über die stufenweise Quaternisierung, etc." Helvetica Chimica Acta vol. XXXIV, 1951, pp. 924–931.
Buyanov V. CA 108(13):105937n (1987).
Kharkwich et al. CA 96(9)62584j (1981).

*Primary Examiner*—Richard L. Raymond
*Assistant Examiner*—Peter G. O'Sullivan
*Attorney, Agent, or Firm*—Alexander J. McKillop; Dennis P. Santini; Robert B. Furr, Jr.

[57] ABSTRACT

The invention provides a composition of matter selected from the group consisting of $$\text{Di}-\underset{\underset{R_1}{|}}{N}-(CH_2)_n-\underset{\underset{R_2}{|}}{N}-\text{Di},$$

$$\text{Di}-\underset{\underset{R_1}{|}}{N}-(CH_2)_n-\underset{\underset{R_2}{|}}{N}-R_3,$$

$$\text{Di}-\underset{\underset{R_1}{|}}{N}-(CH_2)_n-\underset{\underset{R_2}{|}}{N}-(CH_2)_m-\underset{\underset{R_3}{|}}{N}-\text{Di},$$

and

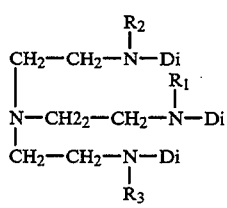

wherein $R_1$, $R_2$, $R_3$, and $R_4$ are selected from the group consisting of hydrogen and alkyl substituent groups having from 1 to about 8 carbon atoms, n is from 2 to about 20, m is from 2 to about 20, and Di is a substituted or unsubstituted diamondoid compound. The invention further provides diamondoid-containing ammonium salts, and a pharmaceutical treatment method using the compositions of the invention.

3 Claims, 6 Drawing Sheets

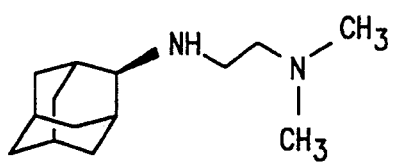
FIG. 4A
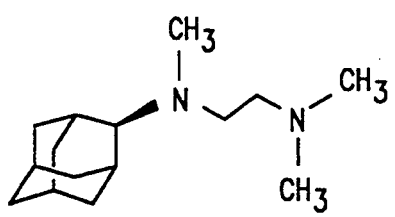
FIG. 4B
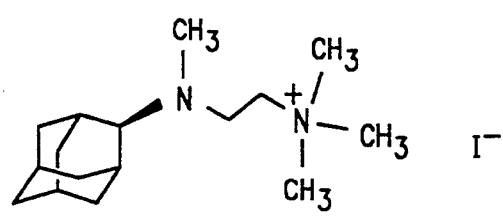
FIG. 4C
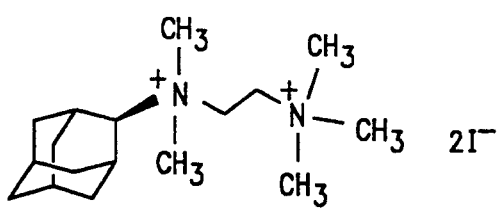
FIG. 4D
FIG. 5A
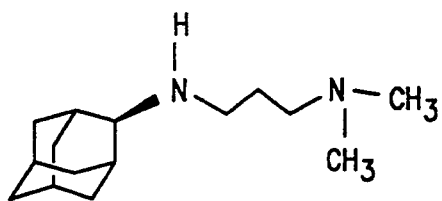
FIG. 5B
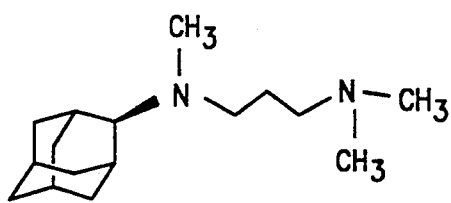
FIG. 6A
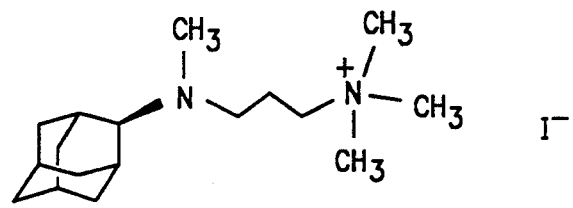
FIG. 6B
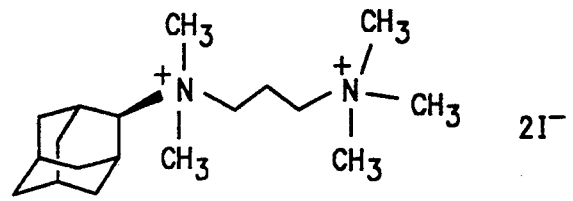

DIAMONDOID-CONTAINING AMINES

CROSS-REFERENCE TO RELATED APPLICATIONS

This is a continuation-in-part of application Ser. No. 07/943,644, filed Sep. 11, 1992 now U.S. Pat. No. 5,256,394.

FIELD OF THE INVENTION

This invention relates to diamondoid-containing amines. Members of this group of compounds are useful as pharmeceuticals and as directing agents for synthesizing inorganic porous solids.

BACKGROUND OF THE INVENTION

Porous inorganic solids have found great utility as catalysts and separations media for industrial application. The openness of their microstructure allows molecules access to the relatively large surface areas of these materials that enhance their catalytic and sorptive activity. The porous materials in use today can be sorted into three broad categories using the details of their microstructure as a basis for classification. These categories are the amorphous and paracrystalline supports, the crystalline molecular sieves and modified layered materials. The detailed differences in the microstructures of these materials manifest themselves as important differences in the catalytic and sorptive behavior of the materials, as well as in differences in various observable properties used to characterize them, such as their surface area, the sizes of pores and the variability in those sizes, the presence or absence of X-ray diffraction patterns and the details in such patterns, and the appearance of the materials when their microstructure is studied by transmission electron microscopy and electron diffraction methods.

Amorphous and paracrystalline materials represent an important class of porous inorganic solids that have been used for many years in industrial applications. Typical examples of these materials are the amorphous silicas commonly used in catalyst formulations and the paracrystalline transitional aluminas used as solid acid catalysts and petroleum reforming catalyst supports. The term "amorphous" is used here to indicate a material with no long range order and can be somewhat misleading, since almost all materials are ordered to some degree, at least on the local scale. An alternate term that has been used to describe these materials is "X-ray indifferent". The microstructure of the silicas consists of 100–250 angstrom particles of dense amorphous silica (*Kirk-Othmer Encyclopedia of Chemical Technology*, 3rd Edition, Vol. 20, John Wiley & Sons, New York, p. 766–781, 1982), with the porosity resulting from voids between the particles. Since there is no long range order in these materials, the pores tend to be distributed over a rather large range. This lack of order also manifests itself in the X-ray diffraction pattern, which is usually featureless.

Paracrystalline materials such as the transitional aluminas also have a wide distribution of pore sizes, but better defined X-ray diffraction patterns usually consisting of a few broad peaks. The microstructure of these materials consists of tiny crystalline regions of condensed alumina phases and the porosity of the materials results from irregular voids between these regions (K. Wefers and Chanakya Misra, "Oxides and Hydroxides of Aluminum", Technical Paper No. 19 Revised, Alcoa Research Laboratories, p. 54–59, 1987). Since, in the case of either material, there is no long range order controlling the sizes of pores in the material, the variability in pore size is typically quite high. The sizes of pores in these materials fall into a regime called the mesoporous range, which, for the purposes of this application, is from about 13 to 200 angstroms.

In sharp contrast to these structurally ill-defined solids are materials whose pore size distribution is very narrow because it is controlled by the precisely repeating crystalline nature of the materials' microstructure. These materials are called "molecular sieves", the most important examples of which are zeolites.

Zeolites, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials are known as "molecular sieves" and are utilized in a variety of ways to take advantage of these properties.

Such molecular sieves, both natural and synthetic, include a wide variety of positive ion-containing crystalline silicates. These silicates can be described as a rigid three-dimensional framework of $SiO_4$ and Periodic Table Group IIIB element oxide, e.g. $AlO_4$, in which the tetrahedra are cross-linked by the sharing of oxygen atoms whereby the ratio of the total Group IIIB element, e.g. aluminum, and Group IVB element, e.g. silicon, atoms to oxygen atoms is 1:2. The electrovalence of the tetrahedra containing the Group IIIB element, e.g. aluminum, is balanced by the inclusion in the crystal of a cation, for example, an alkali metal or an alkaline earth metal cation.

This can be expressed wherein the ratio of the Group IIIB element, e.g. aluminum, to the number of various cations, such as $Ca/2$, $Sr/2$, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite A (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the SiO$_2$/Al$_2$O$_3$ ratio is unbounded. ZSM-5 is one such example wherein the SiO$_2$/Al$_2$O$_3$ ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865 and 4,104,294 describe crystalline silicate of varying alumina and metal content.

Aluminum phosphates are taught in U.S. Pat. Nos. 4,310,440 and 4,385,994, for example. These aluminum phosphate materials have essentially electroneutral lattices. U.S. Pat. No. 3,801,704 teaches an aluminum phosphate treated in a certain way to impart acidity.

An early reference to a hydrated aluminum phosphate which is crystalline until heated at about 110° C., at which point it becomes amorphous or transforms, is the "H$_1$" phase or hydrate of aluminum phosphate of F.d'Yvoire, *Memoir Presented to the Chemical Society*, No. 392, "Study of Aluminum Phosphate and Trivalent Iron", Jul. 6, 1961 (received), pp. 1762-1776. This material, when crystalline, is identified by the JCPDS International Center for Diffraction Data card number 15-274. Once heated at about 110° C., however, the d'Yvoire material becomes amorphous or transforms to the aluminophosphate form of tridymite.

Compositions comprising crystals having a framework topology after heating at 110° C. or higher giving an X-ray diffraction pattern consistent with a material having pore windows formed by 18 tetrahedral members of about 12-13 angstroms in diameter are taught in U.S. Pat. No. 4,880,611.

A naturally occurring, highly hydrated basic ferric oxyphosphate mineral, cacoxenite, is reported by Moore and Shen, *Nature*, Vol. 306, No. 5941, pp. 356-358 (1983) to have a framework structure containing very large channels with a calculated free pore diameter of 14.2 angstroms. R. Szostak et al., *Zeolites: Facts, Figures, Future*, Elsevier Science Publishers B. V., 1989, present work showing cacoxenite as being very hydrophilic, i.e. adsorbing non-polar hydrocarbons only with great difficulty. Their work also shows that thermal treatment of cacoxenite causes an overall decline in X-ray peak intensity.

Silicoaluminophosphates of various structures are taught in U.S. Pat. No. 4,440,871. Aluminosilicates containing phosphorous, i.e. silicoaluminophosphates of particular structures are taught in U.S. Pat. Nos. 3,355,246 (i.e. ZK-21) and 3,791,964 (i.e. ZK-22). Other teachings of silicoaluminophosphates and their synthesis include U.S. Pat. Nos. 4,673,559 (two-phase synthesis method); 4,623,527 (MCM-10); 4,639,358 (MCM-1); 4,647,442 (MCM-2); 4,664,897 (MCM-4); 4,638,357 (MCM-5); and 4,632,811 (MCM-3).

A method for synthesizing crystalline metalloaluminophosphates is shown in U.S. Pat. No. 4,713,227, and an antimonophosphoaluminate and the method for its synthesis are taught in U.S. Pat. No. 4,619,818. U.S. Pat. No. 4,567,029 teaches metalloaluminophosphates, and titaniumaluminophosphate and the method for its synthesis are taught in U.S. Pat. No. 4,500,651.

The phosphorus-substituted zeolites of Canadian Patents 911,416; 911,417; and 911,418 are referred to as "aluminosilicophosphate" zeolites. Some of the phosphorus therein appears to be occluded, not structural.

U.S. Pat. No. 4,363,748 describes a combination of silica and aluminum-calcium-cerium phosphate as a low acid activity catalyst for oxidative dehydrogenation. Great Britain Patent 2,068,253 discloses a combination of silica and aluminum-calcium-tungsten phosphate as a low acid activity catalyst for oxidative dehydrogenation. U.S. Pat. No. 4,228,036 teaches an alumina-aluminum phosphate-silica matrix as an amorphous body to be mixed with zeolite for use as cracking catalyst. U.S. Pat. No. 3,213,035 teaches improving hardness of aluminosilicate catalysts by treatment with phosphoric acid. The catalysts are amorphous.

Other patents teaching aluminum phosphates include U.S. Pat. Nos. 4,365,095; 4,361,705; 4,222,896; 4,210,560; 4,179,358; 4,158,621; 4,071,471; 4,014,945; 3,904,550; and 3,697,550.

The precise crystalline microstructure of most zeolites manifests itself in a well-defined X-ray diffraction pattern that usually contains many sharp maxima and that serves to uniquely define the material. Similarly, the dimensions of pores in these materials are very regular, due to the precise repetition of the crystalline microstructure. All molecular sieves discovered to date have pore sizes in the microporous range, which is usually quoted as 2 to 20 angstroms, with the largest reported being about 12 angstroms.

Certain layered materials, which contain layers capable of being spaced apart with a swelling agent, may be pillared to provide materials having a large degree of porosity. Examples of such layered materials include clays. Such clays may be swollen with water, whereby the layers of the clay are spaced apart by water molecules. Other layered materials are not swellable with water, but may be swollen with certain organic swelling agents such as amines and quaternary ammonium compounds. Examples of such non-water swellable layered materials are described in U.S. Pat. No. 4,859,648 and include layered silicates, magadiite, kenyaite, tritita-nates and perovskites. Another example of a non-water swellable layered material, which can be swollen with certain organic swelling agents, is a vacancy-containing titanometallate material, as described in U.S. Pat. No. 4,831,006.

Once a layered material is swollen, the material may be pillared by interposing a thermally stable substance, such as silica, between the spaced apart layers. The aforementioned U.S. Pat. Nos. 4,831,006 and 4,859,648 describe methods for pillaring the non-water swellable layered materials described therein and are incorporated herein by reference for definition of pillaring and pillared materials.

Other patents teaching pillaring of layered materials and the pillared products include U.S. Pat. Nos. 4,216,188; 4,248,739; 4,176,090; and 4,367,163; and European Patent Application 205,711.

The X-ray diffraction patterns of pillared layered materials can vary considerably, depending on the degree that swelling and pillaring disrupt the otherwise usually well-ordered layered microstructure. The regularity of the microstructure in some pillared layered materials is so badly disrupted that only one peak in the low angle region on the X-ray diffraction pattern is observed, as a d-spacing corresponding to the interlayer repeat in the pillared material. Less disrupted materials may show several peaks in this region that are generally orders of this fundamental repeat. X-ray reflections from the crystalline structure of the layers are also sometimes observed. The pore size distribution in these pillared layered materials is narrower than those in amorphous and paracrystalline materials but broader than that in crystalline framework materials.

The synthetic porous inorganic materials are generally produced from a reaction mixture (or "gel") which contains the precursors of the synthetic material. Because the necessary seed crystals may be unavailable (particularly when the porous inorganic material is new and has not previously been synthesized) it would be desirable to provide a synthesis method which generates a selected porous inorganic material from a particular reaction mixture containing no nucleating seeds.

The reaction mixture for a particular porous inorganic material may also contain an organic directing agent or templating agent. The terms "templating agent" and "directing agent" are both used to describe compounds (usually organics) added to the reaction mixture to promote formation of the desired porous inorganic solid.

Bulky organic bases which are favored as directing agents include cetyltrimetylammonium (CTMA), myristyltrimethylammonium ($C_{14}TMA$), decyltrimethylammonium, cetyltrimethylphosphonium, octadecyltrimethylphosphonium, benzyltrimethylammonium, cetylpyridinium, dodecyltrimethylammonium, and dimethyldidodecylammonium, merely to name a few. The templating action of various organic entitles is also discussed in A. Dyer *An Introduction to Zeolite Molecular Sieves* 60 (1988), as well as in B. M. Lok et al., The Role of Organic Molecules in Molecular Sieve Synthesis 3 *Zeolites* 282 (1983), which are incorporated by reference as if set forth at length herein. These materials are costly, and usually account for most of the materials-related expense in the synthesis of inorganic porous solids.

U.S. Pat. No. 4,665,110 to Zones teaches a process for preparing molecular sieves using an adamantane-derived template. U.S. Pat. No. 4,826,667 to Zones teaches a method for making zeolite SSZ-25 using an adamantane quaternary ammonium ion as a template.

U.S. Pat. No. 4,657,748 to Vaughan and Strohmaier discloses the zeolite ECR-1. For a discussion of a proposed structure of zeolite ECR-1, see M. E. Leonowicz and D. E. W. Vaughan, "Proposed synthetic zeolite ECR-1 structure gives a new zeolite framework topology", Nature, Vol. 329, No. 6142, pages 819–821 (October, 1987).

Adamantane, tricyclo-[$3.3.1.1^{3,7}$]decane, is a polycyclic alkane with the structure of three fused cyclohexane rings. Adamantane has been found to be a useful building block in the synthesis of a broad range of organic compounds. The ten carbon atoms which define the framework structure of adamantane are arranged in an essentially strainless manner. Four of these carbon atoms, the bridgehead carbons, are tetrahedrally disposed about the center of the molecule. The other six (methylene carbons) are octahedrally disposed. U.S. Pat. Nos. 5,019,660 to Chapman and Whitehurst and 5,053,434 to Chapman teach diamondoid compounds which bond through the methylene positions of various diamondoid compounds, including adamantane. For a survey of the chemistry of diamondoid molecules, see *Adamantane, The Chemistry of Diamond Molecules*, Raymond C. Fort, Marcel Dekker, New York, 1976.

Many hydrocarbonaceous mineral streams contain some small proportion of diamondoid compounds. These high boiling, saturated, three-dimensional polycyclic organics are illustrated by adamantane, diamantane, triamantane and various side chain substituted homologues, particularly the methyl derivatives. These compounds have high melting points and high vapor pressures for their molecular weights and have recently been found to cause problems during production and refining of hydrocarbonaceous minerals, particularly natural gas, by condensing out and solidifying, thereby clogging pipes and other pieces of equipment.

In recent times, new sources of hydrocarbon minerals have been brought into production which, for some unknown reason, have substantially larger concentrations of diamondoid compounds. Whereas in the past, the amount of diamondoid compounds has been too small to cause operational problems such as production cooler plugging, now these compounds represent both a larger problem and a larger opportunity. The presence of diamondoid compounds in natural gas has been found to cause plugging in the process equipment requiring costly maintenance downtime to remove. On the other hand, these very compounds which can deleteriously affect the profitability of natural gas production are themselves valuable products.

The problem of deposition and plugging by solid diamondoids in natural gas production equipment has been successfully addressed by a controlled solvent injection process. U.S. Pat. No. 4,952,748 to Alexander and Knight teaches the process for extracting diamondoid compounds from a hydrocarbon gas stream by contacting the diamondoid-laden hydrocarbon gas with a suitable solvent to preferentially dissolve the diamondoid compounds into the solvent. U.S. Pat. No. 5,120,899 to Chen and Wentzek teaches a particularly useful method for sorbing and isolating diamondoid fractions.

Further studies have revealed that separation of the diamondoid compounds from the diamondoid-enriched solvent is complicated by the fact that numerous diamondoid compounds boil in a narrow range of temperatures surrounding the boiling range of the most preferred solvents. U.S. Pat. Nos. 4,952,747, 4,952,749, and 4,982,049 to Alexander et al. teach various methods of concentrating diamondoid compounds in the solvent for, among other reasons, recycling the lean solvent fraction for reuse. Each of these processes produces an enriched solvent stream containing a mixture of diamondoid compounds. The above-listed U.S. Patents are incorporated by reference as if set forth at length herein for the details of recovering and concentrating diamondoid compounds.

SUMMARY OF THE INVENTION

This invention provides a composition of matter selected from the group consisting of

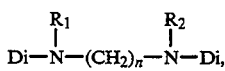

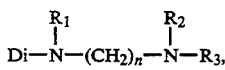

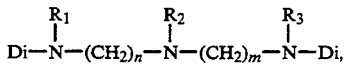

and

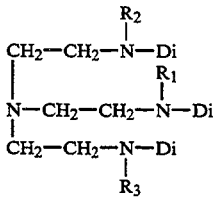

wherein $R_1$, $R_2$, $R_3$, and $R_4$ are selected from the group consisting of hydrogen and alkyl substituent groups having from 1 to about 8 carbon atoms, n is from 2 to about 20, m is from 2 to about 20, and Di is a substituted or unsubstituted diamondoid compound.

This invention further comprises diamondoid-containing ammonium salts including mono-, di-, and tri-quaternary ammonium salts. The ammonium salts of the invention include compositions of matter selected from the group consisting of:

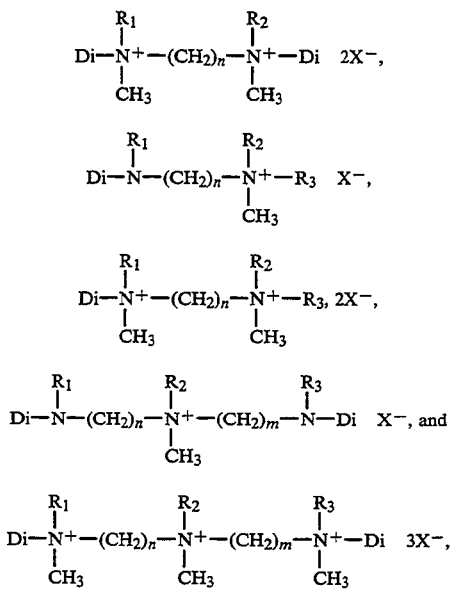

wherein $R_1$, $R_2$, $R_3$, and $R_4$ are selected from the group consisting of alkyl substituent groups having from 1 to about 8 carbon atoms, n is from 2 to about 20, m is from 2 to about 20, Di is a substituted or unsubstituted diamondoid compound, and X is a halogen.

The compositions of the present invention are useful as directing agents in an improved method for synthesis of a porous inorganic solid comprising forming a reaction mixture containing water, an alumina source, a silica source, an alkali metal oxide source, and a diquaternary ammonium salt having the formula

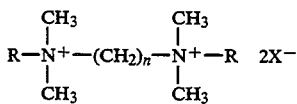

wherein R is a diamondoid group and n is from about 1 to about 50, preferably from about 1 to about 20, more preferably from about 2 to about 12, and wherein X is an anion which is not detrimental to the formation of the porous inorganic solid, and is preferably a halogen or hydroxide, more preferably $I^-$. This synthesis method is taught in allowed U.S. application Ser. No. 07/943,644, filed Sep. 11, 1992, which is incorporated by reference as if set forth at length herein. Porous inorganic solids which may be synthesized in using the compounds of the invention as directing agents are also listed in the Background section, above, and are incorporated by reference as if set forth at length herein.

The compounds of this invention have been found to possess valuable pharmacological properties for both human and vetinary medicine. The compounds have been found to display antiviral effects, and are believed to be useful both in the prevention and chemoprophylaxis of viral illnesses. The compounds are also believed to be useful in the treatment of idiopathic Parkinson's Disease, postencephalitic parkinsonism, and symptomatic parkinsonism resulting from damage to the nervous system caused by carbon monoxide intoxication as well as in the treatment of parkinsonism associated with cerebral arteriosclerosis, particularly in elderly patients.

These compounds can also be used to treat cardic, circulatory and vascular diseases, especially cardiac insufficiency; depression; hypertension; drug-induced extrapyramidal reactions; bacterial infections; and viral infections. These compounds are particularly useful as antivirals.

In addition, the compounds can be used in in vitro diagnostics (e.g., in an assay for renin, bacteria, virus, etc.). They can be employed in admixture with carriers, germicides, fungitides, or soaps, etc., for use as antiseptic solutions and the like, particularly in conjunction with hospital housekeeping procedures, e.g., to combat HIV. The compounds of the invention are also useful as intermediates to synthesize other pharmeceuticals such as functionalized triamines, tetraamines, and higher functionalized diamondcid-containing amines and their derivatives.

The compounds of this invention are generally administered to animals, including mammals, fish, reptiles, and avians, more preferably to mammals including humans, livestock, cattle, poultry, and household pets including cats and dogs.

The pharmacologically active compounds of this invention can be processed in accordance with conventional methods of galenic pharmacy to produce medicinal agents for administration to patients, e.g., mammals including humans.

The compounds of this invention can be employed in admixture with conventional excipients, i.e., pharmaceutically acceptable organic or inorganic carrier substances suitable for parenteral, enteral (e.g., oral) or topical application which do not deleteriously react with the active compounds. Suitable pharmeceutically acceptable carriers include but are not limited to water, salt solutions, alcohols, gum arabic, vegetable oils, benzyl alcohols, polyethylene glycols, gelatine, carbohydrates such as lactose, amylose, or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, merely to name a few. The pharmaceutical preparations can be sterilized and if desired mixed with auxiliary agents, e.g., lubricants, preservatives, mixed with auxiliary agents, e.g., lubricants, preservatives, stabilizers, wetting agents, emulsifiers, salts for influencing osmotic pressure, buffers, coloring, flavoring, and/or aromatic substances and the like which do not deleteriously react with the active compounds.

They can also be combined where desired with other active agents, e.g., vitamins.

For parenteral application, particularly suitable are injectable, sterile solutions, preferably oily or aqueous solutions, as well as suspensions, emulsions, or implants including suppositories. Ampoules are convenient unit dosages.

For enteral application, particularly suitable are tablets, dragees, liquids, drops, suppositories, or capsules. A syrup, elixir, or the like can be used wherein a sweetened vehicle is employed.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lypophilizates obtained, for example, for the preparation of products for injection.

For topical application, there are employed as nonsprayable forms, viscous to semi-solid or solid forms comprising a carrier compatible with topical application and having a dynamic viscosity preferably greater than water. Suitable formulations include but are not limited to solutions, suspensions, emulsions, creams, ointments, powders, liniments, salves, aerosols, etc., which are, if desired, sterilized or mixed with auxiliary agents, e.g., preservatives, stabilizers, wetting agents, buffers, or salts for influencing osmotic pressure, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

Generally the compounds of this invention are dispensed in unit dosage form comprising from 10 to 300 mg in a pharmaceutically acceptable carrier per unit dosage. They are incorporated in topical formulations in concentrations of from about 0.01 to about 3 weight percent.

The dosage of the compounds according to this invention generally is from about 10 to about 1000 mg/day, preferably 50 to 300 mg/day, when administered to patients, e.g., humans, as an antiviral analagously to Symmetrel brand amantadine hydrochloride, which is commercially available from DuPont Pharmeceuticals, Inc., Wilmington, Del., 19880.

It will be appreciated that the actual preferred amounts of active compound in a specified case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate convention pharmacological protocol.

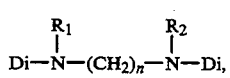

wherein Di is adamantane and $R_1$ and $R_2$ are hydrogen.

Figure 1A:
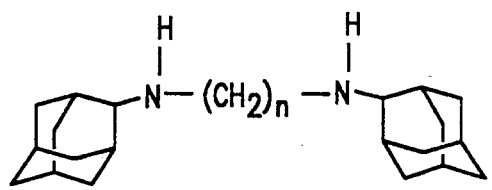
FIG. 1A is an embodiment of the composition of the invention having the formula
Figure 1B:
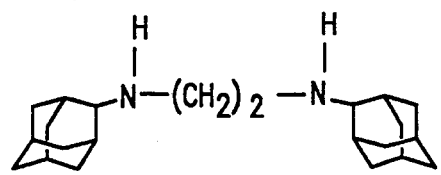

FIG. 1B is an embodiment of the composition of the invention having the formula

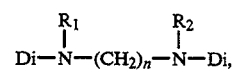

wherein Di is adamantane, $R_1$ and $R_2$ are hydrogen, and n is 2.

Figure 1C:
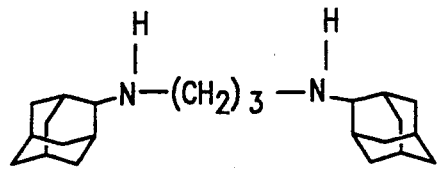

FIG. 1C is an embodiment of the composition of the invention having the formula

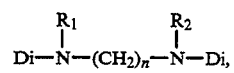

wherein Di is adamantane, $R_1$ and $R_2$ are hydrogen, and n is 3.

Figure 1D:
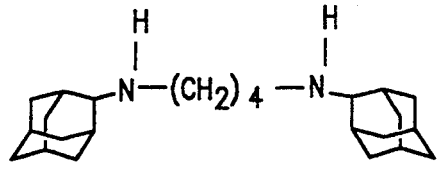

FIG. 1D is an embodiment of the composition of the invention having the formula

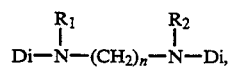

wherein Di is adamantane, $R_1$ and $R_2$ are hydrogen, and n is 4.

Figure 1E:
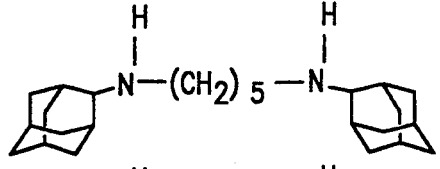

FIG. 1E is an embodiment of the composition of the invention having the formula

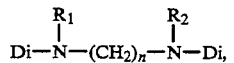

wherein Di is adamantane, $R_1$ and $R_2$ are hydrogen, and n is 5.

Figure 1F:
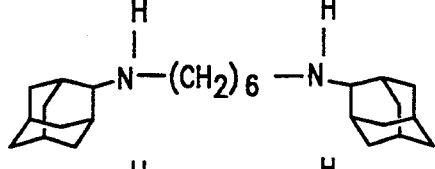

FIG. 1F is an embodiment of the composition of the invention having the formula

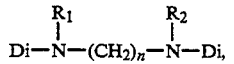

wherein Di is adamantane, $R_1$ and $R_2$ are hydrogen, and n is 6.

Figure 1G:
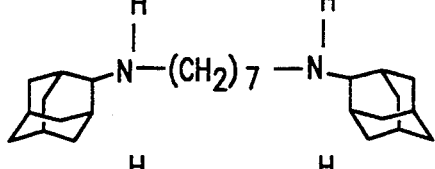

FIG. 1G is an embodiment of the composition of the invention having the formula

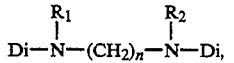

wherein Di is adamantane, $R_1$ and $R_2$ are hydrogen, and n is 7.

Figure 1H:
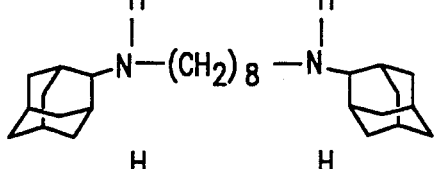

FIG. 1H is an embodiment of the composition of the invention having the formula

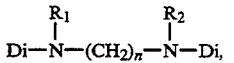

wherein Di is adamantane, $R_1$ and $R_2$ are hydrogen, and n is 8.

Figure 1I:
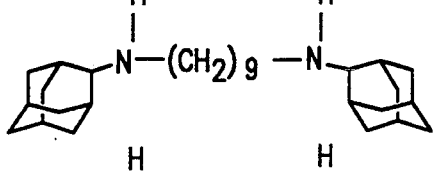

FIG. 1I is an embodiment of the composition of the invention having the formula

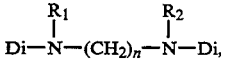

wherein Di is adamantane, $R_1$ and $R_2$ are hydrogen, and n is 9.

Figure 1J:
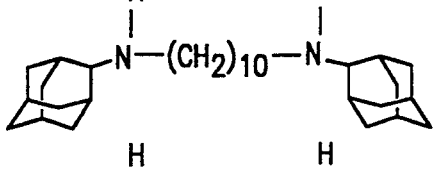

FIG. 1J is an embodiment of the composition of the invention having the formula

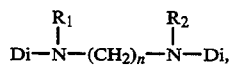

wherein Di is adamantane, $R_1$ and $R_2$ are hydrogen, and n is 10.

Figure 1K:
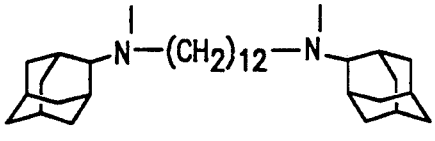

FIG. 1K is an embodiment of the composition of the invention having the formula

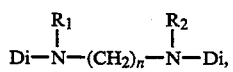

wherein Di is adamantane, $R_1$ and $R_2$ are hydrogen, and n is 12.

Figure 2A:
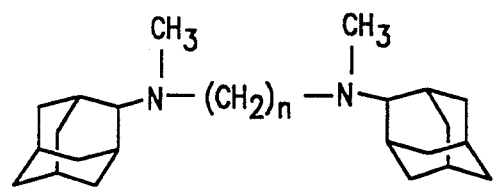

FIG. 2A is an embodiment of the composition of the invention having the formula

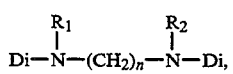

wherein Di is adamantane and $R_1$ and $R_2$ are $CH_3$.

Figure 2B:
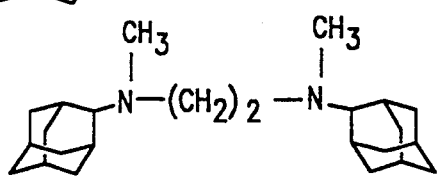

FIG. 2B is an embodiment of the composition of the invention having the formula

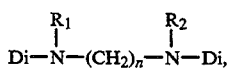

wherein Di is adamantane, $R_1$ and $R_2$ are $CH_3$, and n is 2.

Figure 2C:
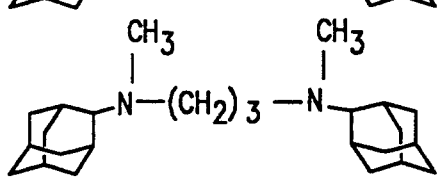

FIG. 2C is an embodiment of the composition of the invention having the formula

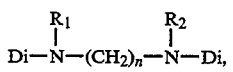

wherein Di is adamantane, $R_1$ and $R_2$ are $CH_3$, and n is 3.

Figure 2D:
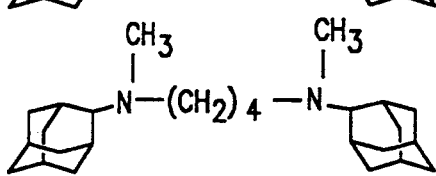

FIG. 2D is an embodiment of the composition of the invention having the formula

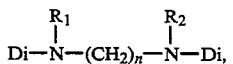

wherein Di is adamantane, $R_1$ and $R_2$ are $CH_3$, and n is 4.

Figure 2E:
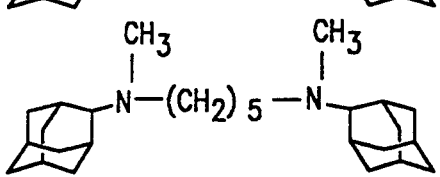

FIG. 2E is an embodiment of the composition of the invention having the formula

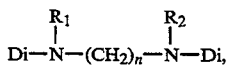

wherein Di is adamantane, $R_1$ and $R_2$ are $CH_3$, and n is 5.

Figure 2F:
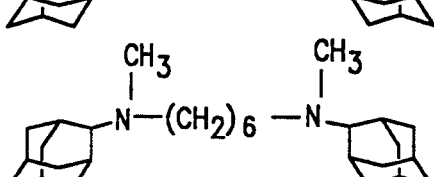

FIG. 2F is an embodiment of the composition of the invention having the formula

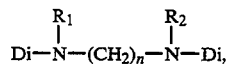

wherein Di is adamantane, $R_1$ and $R_2$ are $CH_3$, and n is 6.

Figure 2G:
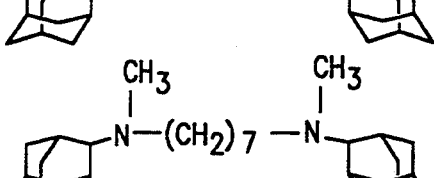

FIG. 2G is an embodiment of the composition of the invention having the formula

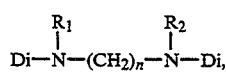

wherein Di is adamantane, $R_1$ and $R_2$ are $CH_3$, and n is 7.

Figure 2H:
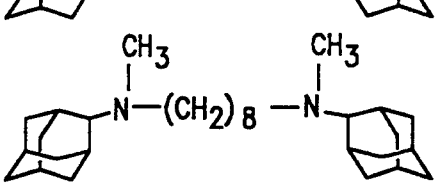

FIG. 2H is an embodiment of the composition of the invention having the formula

wherein Di is adamantane, $R_1$ and $R_2$ are $CH_3$, and n is 8.

Figure 2I:
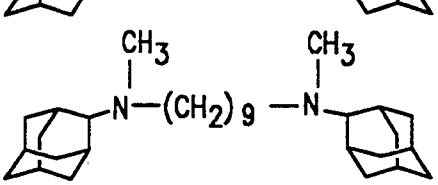

FIG. 2I is an embodiment of the composition of the invention having the formula

wherein Di is adamantane, $R_1$ and $R_2$ are $CH_3$, and n is 9.

Figure 2J:
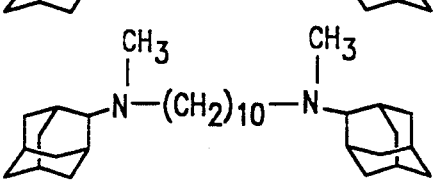

FIG. 2J is an embodiment of the composition of the invention having the formula

wherein Di is adamantane, $R_1$ and $R_2$ are $CH_3$, and n is 10.

Figure 2K:
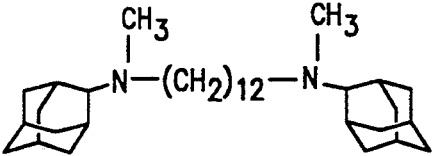

FIG. 2K is an embodiment of the composition of the invention having the formula

wherein Di is adamantane, $R_1$ and $R_2$ are $CH_3$, and n is 12.

Figures 3A, 3B, 3C, 3D, 3E, 3F, 3G, 3H, 3I, 3J, 3K:
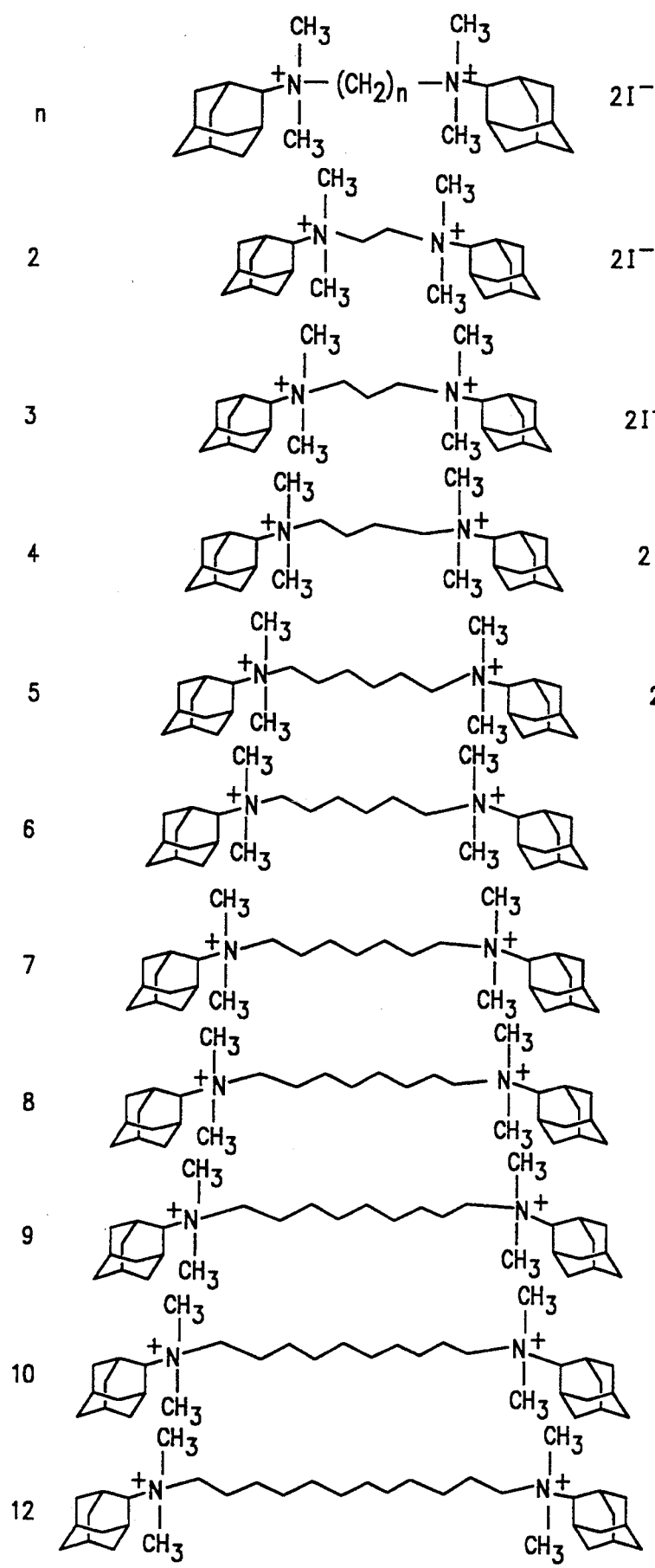

FIG. 3A is a diquaternary ammonium salt of the invention having the formula

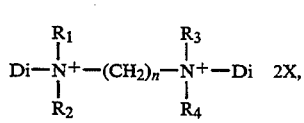

wherein Di is adamantane, $R_1$, $R_2$, $R_3$, and $R_4$ are $CH_3$, and X is iodine.

FIG. 3B is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 2, and X is iodine.

FIG. 3C is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 3, and X is iodine.

FIG. 3D is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 4, and X is iodine.

FIG. 3E is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 5, and X is iodine.

FIG. 3F is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 6, and X is iodine.

FIG. 3G is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 7, and X is iodine.

FIG. 3H is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 8, and X is iodine.

FIG. 3I is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 9, and X is iodine.

FIG. 3J is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 10, and X is iodine.

FIG. 3K is a diquaternary ammonium salt of the invention having the formula $$\text{Di}-\overset{R_1}{\underset{R_2}{N^+}}-(CH_2)_n-\overset{R_3}{\underset{R_4}{N^+}}-\text{Di} \quad 2X^-,$$

wherein Di is adamantane, $R_1$, $R_2$, $R_3$, and $R_4$ are $CH_3$, n is 12, and X is iodine.

FIG. 4A is an embodiment of the composition of the invention having the formula $$\text{Di}-\overset{R_1}{\underset{}{N}}-(CH_2)_n-\overset{R_2}{\underset{}{N}}-R_3,$$

wherein $R_1$ is hydrogen, $R_2$ and $R_3$ are $CH_3$, and n is 2.

FIG. 4B is an embodiment of the composition of the invention having the formula $$\text{Di}-\overset{R_1}{\underset{}{N}}-(CH_2)_n-\overset{R}{\underset{}{N}}-R_3,$$

wherein $R_1$, $R_2$ and $R_3$ are $CH_3$, and n is 2.

FIG. 4C is a monoquaternary ammonium salt having the formula $$R_1-\overset{CH_3}{\underset{}{N}}-(CH_2)_n-\overset{CH_3}{\underset{CH_3}{N^+}}-R_2 \quad X^-$$

wherein $R_1$ is an adamantyl group, $R_2$ is $CH_3$, n is 2, and X is iodine.

FIG. 4D is a diquaternary ammonium salt having the formula $$R_1-\overset{CH_3}{\underset{CH_3}{N^+}}-(CH_2)_n-\overset{CH_3}{\underset{CH_3}{N^+}}-R_2 \quad X^-$$

wherein $R_1$ is an adamantyl group, $R_2$ is $CH_3$, n is 2, and X is iodine.

FIG. 5A is an embodiment of the composition of the invention having the formula

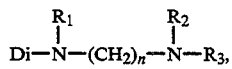

wherein $R_1$ is hydrogen, $R_2$ and $R_3$ are $CH_3$, and n is 3.

FIG. 5B is an embodiment of the composition of the invention having the formula

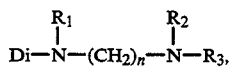

wherein $R_1$, $R_2$ and $R_3$ are $CH_3$, and n is 3.

FIG. 6A is a monoquaternary ammonium salt having the formula

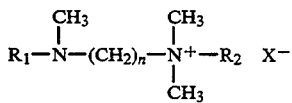

wherein $R_1$ is an adamantyl group, $R_2$ is $CH_3$, n is 3, and X is iodine.

FIG. 6B is a diquaternary ammonium salt having the formula

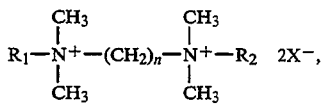

wherein $R_1$ is an adamantyl group, $R_2$ is $CH_3$, n is 3, and X is iodine.

Figure 7A:
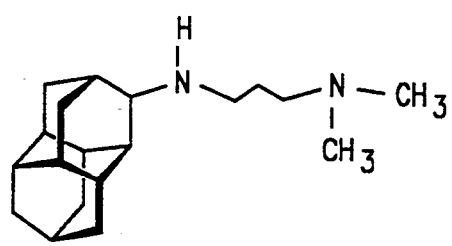

FIG. 7A is an embodiment of the composition of the invention having the formula

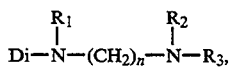

wherein Di is a diamantyl group, $R_1$ is hydrogen, $R_2$ and $R_3$ are $CH_3$, and n is 3.

Figure 7B:
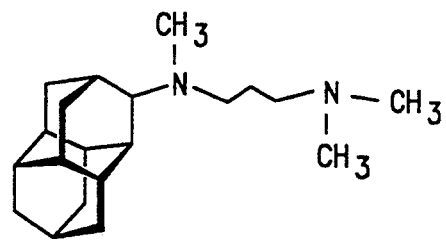

FIG. 7B is an embodiment of the composition of the invention having the formula

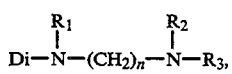

wherein Di is a diamanyl group, $R_1$, $R_2$ and $R_3$ are $CH_3$ and n is 3.

Figure 8A:
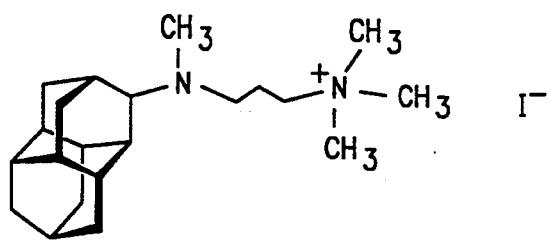

FIG. 8A is a monoquaternary ammonium salt having the formula

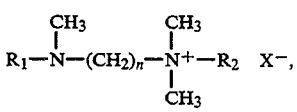

wherein $R_1$ is a diamantyl group, $R_2$ is $CH_3$, n is 3, and X is iodine.

Figure 8B:
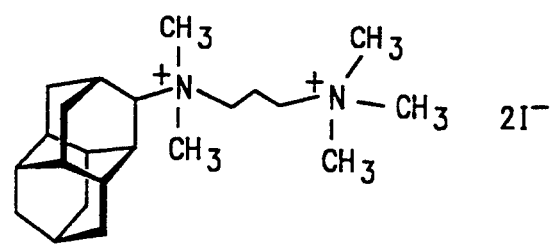

FIG. 8B is a diquaternary ammonium salt having the formula

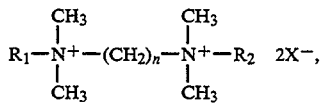

wherein $R_1$ is a diamantyl group, $R_2$ is $CH_3$, n is 3, and X is iodine.

Figure 9A:
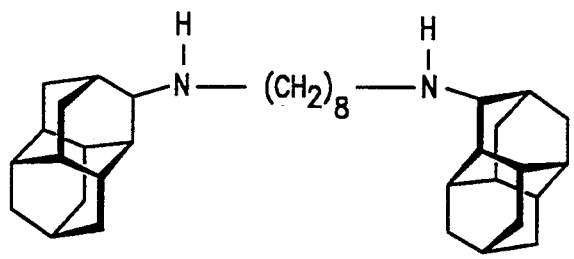

FIG. 9A is an embodiment of the composition of the invention having the formula

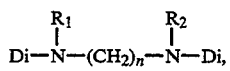

wherein Di is a diamantyl group, $R_1$ and $R_2$ are hydrogen, and n is 8.

Figure 9B:
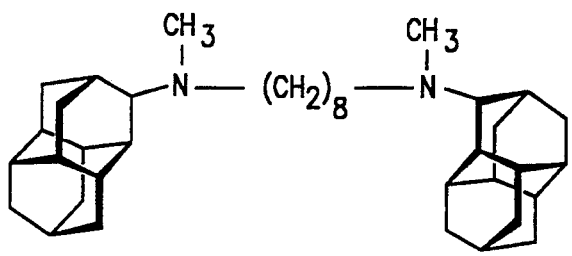

FIG. 9B is an embodiment of the composition of the invention having the formula

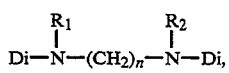

wherein Di is a diamantyl group, $R_1$ and $R_2$ are $CH_3$, and n is 8.

Figure 9C:
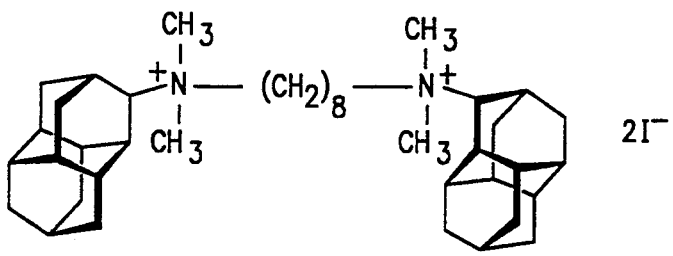

FIG. 9C is a diquaternary ammonium salt having the formula

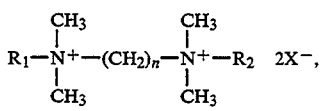

wherein $R_1$ and $R_2$ are diamantyl groups, n is 8, and X is iodine.

Figure 10A:
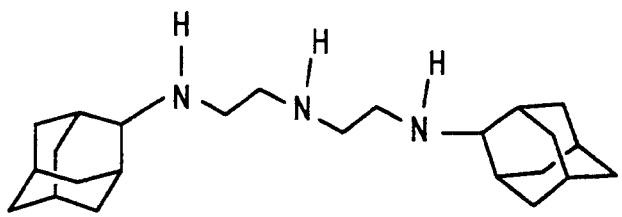

FIG. 10A is an embodiment of the composition of the invention having the formula

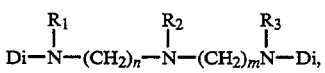

wherein Di is adamantane, $R_1$, $R_2$, and $R_3$, are hydrogen, and n=m=2.

Figure 10B:
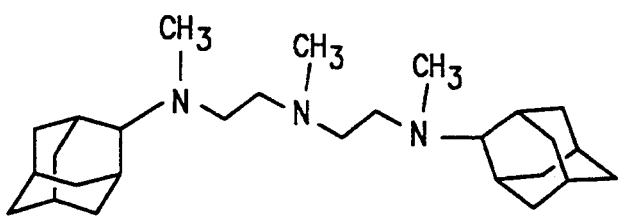

FIG. 10B is an embodiment of the composition of the invention having the formula

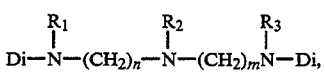

wherein Di is adamantane, $R_1$, $R_2$, and $R_3$, are $CH_3$ and n=m=2.

Figure 10C:
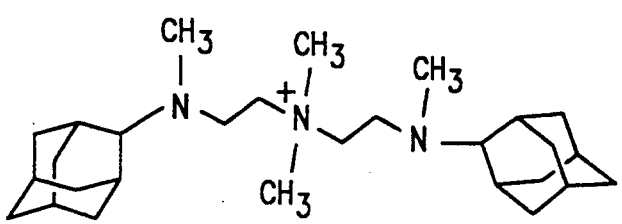

FIG. 10C is a monoquaternary ammonium salt of the invention having the formula

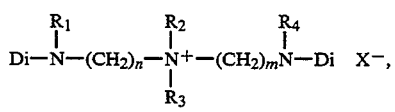

wherein Di is adamantane, $R_1$, $R_2$, $R_3$ and $R_4$ are $CH_3$, and n=m=2.

Figure 10D:
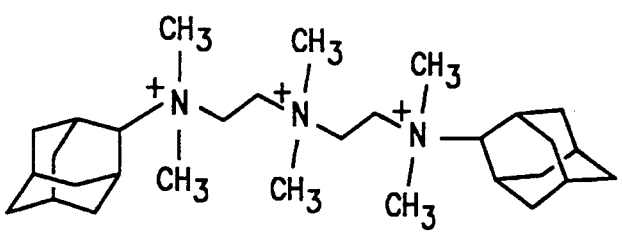

FIG. 10D is a triquaternary ammonium salt of the invention having the formula

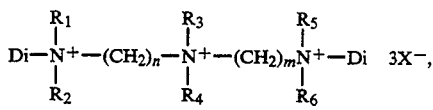

wherein Di is adamantane, $R_1$, $R_2$, $R_3$, $R_4$, $R_5$, and $R_6$ are $CH_3$, $n=m=2$, and X is iodine.

EMBODIMENTS

The diquaternary amine synthesis of the present invention may suitably be synthesized in accordance with the following general procedure which includes the sequential steps of: (1) imine formation between 2-adamantanone or 2-diamantanone and a primary amine, (2) hydrogenation of the imine to the secondary amine, (3) methylation to the tertiary amine and (4) quaternization with methyl iodide. The overall yield to the tertiary amine is typically 90% or higher. The secondary amine can be obtained directly from a primary amine by combining steps (1) and (2) and carrying out a reductive amination. Also, by using reductive amination, the synthesis can start with a secondary amine and produce a tertiary amine directly and with similar high yield. Although the quaternization of adamantyl substituted tertiary amines requires more drastic conditions than the usual mild conditions employed in quaternizations, it typically produces 90% or higher yields from the tertiary amines at 60–90% yield in HPLC grade dimethylformamide in a pressure vessel. By this route, the synthesis of the invention has produced a variety of novel adamantane-containing amines and quaternary ammonium salts of different sizes, shapes, and charge densities. These amines and quaternary ammonium salts are useful as nucleating agents for syntheses of zeolites and other porous catalysts, as well as for pharmaceutical applications as antivirals.

The diquaternary amine may be synthesized in accordance with the following procedure:

(1) Imine Formation Between 2-adamantanone (Or 2-diamantanone) and A Primary Amine: The imine formation was carried out in an appropriate solvent which formed an azeotrope with water to displace the following equilibrium to the right:

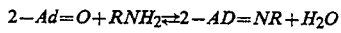

The reaction was carried out in a flask equipped with a mechanical stirrer, a Dean-Stark trap, and a condenser. In general, the reaction was complete in about four hours as evidenced by the calculated amount of water collected in the Dean-Stark trap. When there were more than one primary amino group present in the reactant amine, toluene was used as the solvent because these amines typically had high boiling points. To ensure all the amino groups were to be reacted, a 10% mole excess 2-adamantanone (or 2-diamantanone) was employed. After the reaction the toluene was distilled off and the excess 2-adamantanone (or 2-diamantanone) was removed by sublimation under vacuum. In cases where the amines contained only one primary amino group and were relatively low boiling, cyclohexane was used as the solvent to azeotrope out the produced water, and the amine was used in 20% mole excess. The pot temperature was kept below the boiling point of the amine to prevent the amine from distilling off. After reaction was complete, both cyclohexane and the excess amine were removed by distillation. The structures of the imine products were established by C-13 NMR. The yield based on the reactant not in excess was generally near quantitative. If primary amines only are used as the starting amines, steps (1) and (2) may be combined in a single reductive amination step. The R in the product amine may be tailored to the desired length by adjusting the size and extent of substitution of the R group in the starting amine.

(2) Hydrogenation of Imines to Secondary Amines: The hydrogenation was carried out in ethanol using Pd/C as the catalyst at 50° C. or Ni/Kieselgel as the catalyst at 100° C. Complete hydrogenation took 48–72 hours. The hydrogenated products were generally crystalline or crystallizable from ethanol. The structures of the secondary amines were confirmed by C-13 NMR. The yield from the imine was generally quantitative.

(3) Methylation of Secondary to Tertiary Amine: The methylation step was carried out in accordance with the following general procedure. For a discussion of methylation, see H. W. Geluk and V. G. Keiser, Org. Synthesis, 53, 8, 1973. One mole of a secondary amino group (in these Examples, a molecule often contained more than one secondary amino group) was added slowly to 2.5 moles formic acid (96% in water) in a 2-neck flask equipped with an air-driven mechanical stirrer and a water condenser. Upon stirring, 1.1 moles of formaldehyde (37% in water) were added slowly, followed by the addition of 100 ml water. The mixture was slowly heated to reflux. The solid amine went into solution and gas ($CO_2$) was evolved. The mixture was refluxed overnight until the gas evolution had ceased. Upon cooling, an amount of 195 ml concentrated HCl (36%) was added slowly and the excess formaldehyde and formic acid were driven off at boiling with mechanical stirring while bubbling through a stream of nitrogen. The mixture was cooled down and neutralized with 25% sodium hydroxide solution. The tertiary amine formed was then extracted with ether. The ether extract was washed with water and dried over anhydrous magnesium sulfate. After filtration the ether was distilled off to recover the tertiary amine product. The structure of the product was characterized by C-13 NMR. Yield in this methylation step averaged 90%.

(4) Quaternization: Quaternization of tertiary amino groups, without an adamantyl substituent, required mild conditions under which the adamantyl substituted amino groups are not affected, and was achieved by slowly dropping methyl iodide into an ethanol solution of the amine keeping the temperature under 35° C. The product precipitated out as a solid.

The quaternization of adamantyl substituted tertiary amino groups required more stringent conditions. The presence of any protonic compound either as a solvent or as an impurity resulted in the formation of proton ammonium instead of quaternary ammonium salts. The best solvent was discovered to be HPLC grade (pure) dimethylformamide which was syringed directly into the quaternization reactor to avoid possible exposure to moisture. It was also found to be advantageous to add to the reaction a small amount of anhydrous sodium carbonate. Excess methyl iodide, at a mole ratio of 1.5 $CH_3I$ to 1 amino group and an elevated temperature (60°–90° C.) were required. Due to the low boiling point of $CH_3I$, the reactions were carried out in a Parr reactor. The yield of the quaternization was as high as 90%; however, in some cases other parts of the molecule could degrade (see the following Examples II and III) rendering the overall yield significantly lower.

The following Examples 1–5 illustrate the synthesis of diamondoid-containing diquaternary amines in accordance with the present invention. Examples 1–5 report NMR analyses which are referenced to internal TMS in ppm, measured in $CDCl_3$ or $D_2O$ solvent using an external DSS standard.

| Product | Yield, % | $^{13}C$ NMR | Elemental Analysis |
|---|---|---|---|
| adamantylidene-N-CH₂CH₂-N(CH₃)₂ | 100 | 180.7, 60.9, 48.3, 46.0, 43.9, 39.3, 38.5, 36.7, 33.4, 28.0 | — |
| adamantyl-NH-CH₂CH₂-N(CH₃)₂ | 100 | 62.3, 60.9, 48.3, 45.7, 38.2, 37.8, 32.3, 31.5, 28.0, 27.7 | — |
| adamantyl-N(CH₃)-CH₂CH₂-N(CH₃)₂ | 90 | 67.7, 56.6, 52.4, 46.4, 39.8, 38.2, 37.7, 31.7, 30.0, 27.8, 27.6 | — |
| adamantyl-N(CH₃)-CH₂CH₂-N⁺(CH₃)₃ I⁻ | 90 | 69.3, 63.3, 54.4, 48.5, 41.5, 40.2, 39.7, 33.5, 31.9, 29.2 (2 types) | Calculated for $C_{16}H_{31}N_2I$: C: 50.79; H: 8.26; N: 7.40; I: 33.54 Found: C: 51.13; H: 8.23; N: 7.38; I: 33.81 |
| adamantyl-N⁺(CH₃)₂-CH₂CH₂-N⁺(CH₃)₃ 2I⁻ | 86 | 83.0, 61.4, 59.7, 57.4, 54.5, 42.8, 39.9, 34.2, 31.7, 29.9, 28.7 | Calculated for $C_{17}H_{34}N_2I_2$: C: 39.25; H: 6.59; N: 5.38; I: 48.79 Found: C: 39.02; H: 6.40; N: 5.34; I: 48.23 |

*Yield based on 2-adamantanone

EXAMPLE 1

Starting Materials:

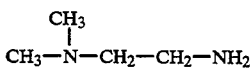

N,N,-Dimethylethylenediamine, 95% 111.4 gm (1.2 moles).
2-Adamantanone, 99%: 151.7 gm (1.0 mole).
Solvent: cyclohexane: 300 ml
Temperature: The pot temperature was kept at about 80° C. and water was azeotroped out at 69° C.
Products:

EXAMPLE 2

Starting Materials:

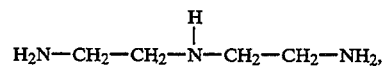

Diethylenetriamine (99%): 104.2 gm (1 mole).
2-Adamantanone (99%): 333.8 gm (2.2 moles).
Solvent: Toluene: 300 ml.
Temperature: Reflux.
Products:

| Product | Yield, % | $^{13}C$ NMR | Elemental Analysis |
|---|---|---|---|
| (adamantylidene-N-CH₂CH₂-)₂NH | 100 | 181.1, 50.8, 49.6, 43.9, 39.4, 38.4, 36.7, 33.5, 27.6 | — |
| (adamantyl-NH-CH₂CH₂-)₂NH | 95 | 62.1, 50.1, 46.8, 38.1, 37.7, 32.3, 31.5, 28.0, 27.8 | — |

5,380,947

-continued

| Product | Yield, % | ¹³C NMR | Elemental Analysis |
|---|---|---|---|
| Bis[N-methyl-N-(2-methylaminoethyl)-2-aminoadamantane] (structure with CH₃ on N, N-CH₃ group, ×2) | 90 | 68.6, 54.9, 52.1, 43.9, 39.9, 38.7, 38.2, 31.6, 30.0, 27.8, 27.5 | — |
| Monoquaternary ammonium iodide (structure with CH₃, N, CH₃/N⁺/CH₃, I⁻, ×2) | 86 | 69.0, 61.6, 52.1, 49.7, 38.5, 37.7, 37.5, 32.1, 30.0, 27.5, 27.4 | Calculated for $C_{28}H_{50}N_3I$: C: 60.53; H: 9.07; N: 7.56; I: 22.84 Found: C: 60.62; H: 9.05; N: 7.64; I: 23.4 |
| Bis-quaternary ammonium triiodide (structure with CH₃/N⁺/CH₃, CH₃/N⁺/CH₃, 3I⁻, ×2) | 54 | 85.1, 62.9, 60.2, 55.5, 55.3, 43.6, 40.6, 34.8, 32.7, 30.6, 29.4 | Calculated for $C_{30}H_{56}N_3I_3$: C: 42.92; H: 6.72; N: 5.00; I: 45.35 Found: C: 42.73; H: 7.08; N: 5.03; I: 45.43 |

*Yield based on diethylenetriamine.

EXAMPLE 3

Starting Materials:

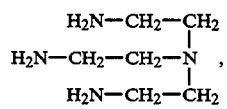

Tris(2-aminoethyl)amine, 99%: 147.7 gm (1 mole).
2-Adamantanone: 99%: 500.7 gm (3.3 moles)
Solvent: Toluene: 300 ml
Temperature: Reflux

Products:

| Product | Yield, % | ¹³C NMR | Elemental Analysis |
|---|---|---|---|
| Tris-imine of adamantanone with tris(2-aminoethyl)amine (×3) | 100 | 180.8, 56.2, 48.2, 43.9, 39.3, 37.5, 33.4, 30.1, 27.9 | — |
| Tris-secondary amine (NH) derivative (×3) | 94 | 62.3, 55.0, 44.9, 38.1, 37.7, 32.3, 31.5, 28.0, 27.8 | — |
| Tris-N-methyl tertiary amine derivative (CH₃ on N, ×3) | 72 | 67.3, 52.1, 52.1, 39.7, 38.0, 37.5, 31.5, 29.9, 27.7, 27.4 | Calculated for $C_{36}H_{60}N_4$: C: 78.78; H: 11.02; N: 10.20 Found: C: 78.88; H: 11.01; N: 10.26 |
| Bis-quaternary ammonium triiodide (CH₃/N⁺/CH₃, CH₃/N⁺/CH₃, 3I⁻, ×2) | 53 | — | Calculated for $C_{30}H_{56}N_3I_3$: C: 42.92; H: 6.72; N: 5.00; I: 45.35 Found: C: 42.73; H: 7.08; N: 5.03; I: 45.43 |

Remarks: Unexpectedly, quaternization of the tertiary amine in this case had resulted in the same quaternary ammonium iodide as in Example II.
*Yield based on tris(2-aminoethyl)amine.

EXAMPLE 4

Starting Materials:

H$_2$N-(CH$_2$)$_6$-NH$_2$, 1,6-diaminohexane, 98%: 118.6 gm (1 mole).

2-Adamantanone, 99%: 333.8 gm (2.2 moles).

Solvent: Toluene: 300 ml

Temperature: Reflux

Products:

| Product | Yield, % | $^{13}$C NMR | Elemental Analysis |
|---|---|---|---|
| 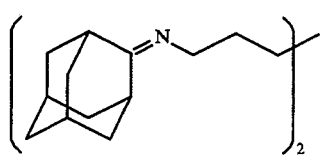 | 100 | — | — |
| 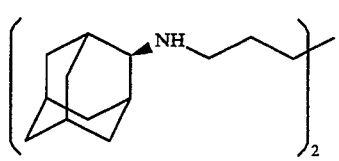 | 95 | 62.0, 47.2, 38.1, 37.8, 32.2, 31.5, 30.7, 28.0, 27.8, 27.6 | — |
| 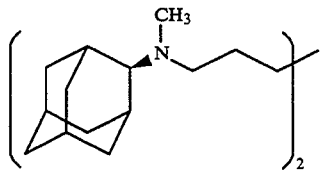 | 90 | 66.9, 53.7, 39.0, 38.0, 37.6, 31.5, 29.8, 27.8, 27.7, 27.5, 24.9 | — |
| 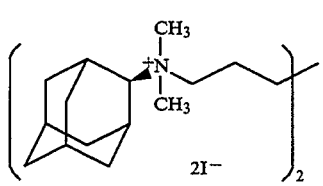 | 83 | 82.1, 69.1, 54.6, 43.7, 40.9, 35.0, 32.5, 30.8, 29.6, 29.1, 25.9 | Calculated for C$_{30}$H$_{54}$N$_2$I$_2$: C: 51.73; H: 7.82; N: 4.02; I: 36.44 Found: C: 51.24; H: 7.91; N: 3.80; I: 36.67 |

*Yield based on 1,6-diaminohexane.

EXAMPLE 5

Starting Materials:

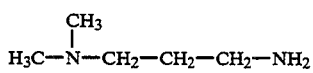

N,N-Dimethylpropylenediamine, 100%: 122.6 gm (1.2 moles)

2-Adamantanone, 99%: 150.7 gm (1 mole).

Solvent: Cyclohexane: 300 ml

Temperature: The pot temperature was 85° C. Water azeotroped out at 69° C.

Products:

| Product | Yield, % | $^{13}$C NMR | Elemental Analysis |
|---|---|---|---|
| 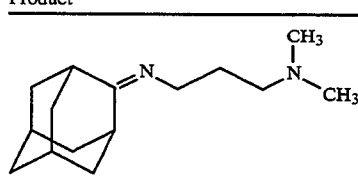 | 97 | 179.9, 58.1, 47.9, 45.7, 43.9, 39.3, 38.4, 36.6, 33.0, 29.5, 27.9 | — |
| 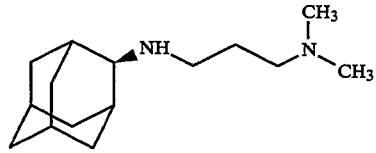 | 97 | 62.3, 58.8, 46.0, 45.9, 38.4, 38.0, 32.3, 31.6, 28.9, 28.1, 27.9 | — |

-continued

| Product | Yield, % | 13C NMR | Elemental Analysis |
|---|---|---|---|
| 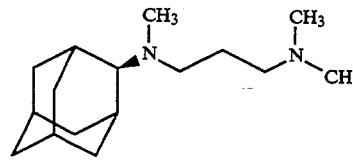 | 74 | 67.3, 58.7, 52.1, 46.0, 39.1, 38.2, 37.8, 31.7, 29.9, 27.8, 27.6, 23.7 | — |
| 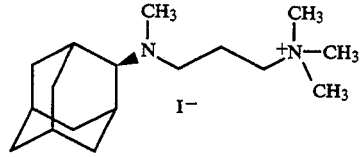 | 69 | 71.0, 68.8, 57.1, 53.4, 42.2, 40.9, 40.7, 34.3, 32.4, 30.4 (2 types of carbons), 20.8 | — |
| 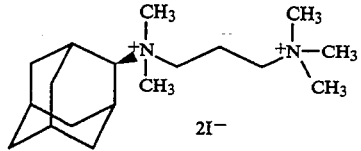 | 70 | 83.1, 66.6, 64.4, 57.4, 54.6, 43.4, 40.6, 34.7, 32.2, 30.5, 29.2, 21.0 | Calculated for $C_{18}H_{36}N_2I_2$: C: 40.46; H: 6.79; N: 5.24; I: 47.50 Found: C: 40.09; H: 6.89; N: 5.19; I: 48.15 |

*Yield based on 2-adamantanone.

EXAMPLE 6

Starting Materials:

$H_2N$-$(CH_2)_8$-$NH_2$, 1,8-diaminooctane, 98%: 36.1 gm (0.25 mole).

2-Diamantanone, 97%: 101.2 gm (0.5 mole).

Solvent: Ethanol: 200 ml

Catalyst for Hydrogenation: Pd (5 wt. %) on activated carbon: 15 grams.

The reagents were mixed in a 600 ml Parr reactor. The reactor was sealed and purged with nitrogen gas, then filled with $H_2$ for reductive amination. The $H_2$ pressure in the reactor was maintained at 500 psig and $H_2$ was continuously fed to the reactor from a reservoir bomb. The reaction was carried out at 75° C. for 72 hours at which time no more $H_2$ was taken up. The product (structural formula shown in FIG. 9A) was isolated from the reaction mixture in 80% yield (103.3 gm) based upon the starting materials. The product (FIG. 9A) was methylated to yield a product having the structure shown in FIG. 9B in 85% yield (92.6 gm) based upon the product of FIG. 9A. The product of FIG. 9B was then quaternized in DMF with 75 gm $CH_3I$ at 75° C. for 72 hours. The reactor was cooled down to ambient temperature and opened. The product (structure shown in FIG. 9C) was washed with DMF first, then with excess hot ethanol until the washing was clear. The product of FIG. 9C was further purified by extracting the product in a thimble in a Soxhet extractor with water. Upon cooling, the product of FIG. 9C crystallized from the aqueous extract as white crystals. The yield for the product of FIG. 9C based upon the product of FIG. 9B was 90% (126.8 grams).

Elemental analysis of the product of FIG. 9C: Calculated for $C_{40}H_{66}N_2I_2$: C: 57.97; H: 8.03; N: 3.38; I:30.63. Found: C: 57.75; H: 8.04; N: 3.38; I:31.08.

EXAMPLE 7

Starting Materials:

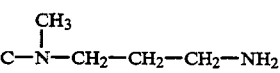

N,N-Dimethylpropylenediamine, 100%: 51.1 gm (0.5 mole)

2-Diamantanone, 97%: 101.2 gm (0.5 mole).

Solvent: Ethanol; 300 ml.

Catalyst for Hydrogenation: Pd (5 wt. %) on activated carbon, 16.0 gm.

The reactants were mixed in a 600 ml Parr reactor. The reactor was sealed and purged with nitrogen gas, then filled with $H_2$ for reductive amination. The $H_2$ pressure in the reactor was maintained at 500 psig and $H_2$ was continuously fed to the Parr reactor from a reservoir bomb. The reaction was carried out at 75° C. for 72 hours at which time no more $H_2$ was taken up. The product (structure shown in FIG. 7A) was isolated in 100% yield (143.7 gm). The product (FIG. 7A) was methylated and 132 gm of product (structure shown in FIG. 7B) was obtained in 84% yield based upon starting materials. The product shown in FIG. 7B was quaternized with 61.9 gm $CH_3I$ at ≦45° C. by adding the $CH_3I$ slowly to obtain a product having the structure shown in FIG. 8A in quantitative yield. The product of FIG. 8A was then subjected to further quaternization in DMF with 93 gm additional $CH_3I$ in a 600 ml Parr reactor at 75° C. for 72 hours. The reactor was cooled down to ambient temperature and opened. The solid crystalline product was first washed with DMF, then with hot ethanol until the washing was clear (≈5 liters). The washed product was white and dried at 75° C./30 mm Hg to 240.2 gm (82% yield based upon starting materials). The initial DMF washing was rotavapped and the solid product was again washed with ethanol to give an additional 4.5 gm of the product of FIG. 8B. The product of FIG. 8B was then recrystallinzed in boiling water and white glistening crystals were obtained from water at room temperature.

Elemental analysis of the product of FIG. 8B: Calculated for $C_{22}H_{40}N_2I_2$: C: 45.06; H: 6.88; N: 4.78; I: 43.29. Found: C: 44.99; H: 6.95; N: 4.72; I: 43.23.

Changes and modifications in the specifically described embodiments can be carried out without departing from the scope of the invention which is intended to be limited only by the scope of the appended claims.

What is claimed is:

1. An unsymmetrical diquaternary ammonium salt selected from the group consisting of:

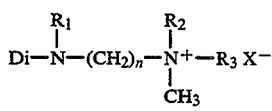

and

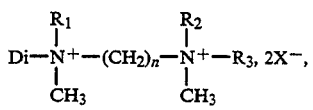

wherein $R_1$, $R_2$, and $R_3$ are selected from the group consisting of hydrogen and alkyl substituent groups having from 1 to about 8 carbon atoms, n is from 2 to about 20, Di is a substituted or unsubstituted diamondoid compound, and X is a halogen.

2. The composition of claim 1 wherein said diamondoid compound is selected from the group consisting of substituted or unsubstituted adamantane and substituted or unsubstituted diamantane.

3. The composition of claim 1 wherein n is from 2 to 10.

* * * * *